US006946021B2

(12) United States Patent
Aoyagi

(10) Patent No.: US 6,946,021 B2
(45) Date of Patent: Sep. 20, 2005

(54) AIR CLEANER

(75) Inventor: Kohei Aoyagi, Tokyo (JP)

(73) Assignee: Kabushiki Kaisha Sunseal, Osaka (JP)

( * ) Notice: Subject to any disclaimer, the term of this patent is extended or adjusted under 35 U.S.C. 154(b) by 88 days.

(21) Appl. No.: 10/752,279

(22) Filed: Jan. 6, 2004

(65) Prior Publication Data

US 2005/0072308 A1 Apr. 7, 2005

(30) Foreign Application Priority Data

Oct. 2, 2003 (JP) ...................................... 2003-344539

(51) Int. Cl.[7] .............................................. B01D 47/06
(52) U.S. Cl. ............................ 96/226; 96/235; 261/117
(58) Field of Search ......................... 96/226, 227, 235, 96/271, 273, 280, 355; 261/117

(56) References Cited

U.S. PATENT DOCUMENTS

| | | | | |
|---|---|---|---|---|
| 3,726,062 A | * | 4/1973 | Hungate et al. ............... | 95/199 |
| 5,989,497 A | * | 11/1999 | Labonte, Jr. ................... | 422/5 |
| 6,363,734 B1 | * | 4/2002 | Aoyagi .......................... | 62/264 |
| 6,451,096 B1 | | 9/2002 | Kim | |
| 6,579,506 B2 | * | 6/2003 | Spink et al. ................... | 423/210 |
| 6,858,181 B2 | * | 2/2005 | Aoyagi .......................... | 422/24 |
| 2004/0013563 A1 | * | 1/2004 | Romer et al. .................. | 422/28 |
| 2004/0237782 A1 | * | 12/2004 | Decker .......................... | 95/211 |

* cited by examiner

Primary Examiner—Frank M. Lawrence
(74) Attorney, Agent, or Firm—Pitney Hardin LLP

(57) ABSTRACT

An air cleaner for cleaning air and for providing sterilization and deodorization effects, includes an air-liquid contact part, for bringing the air into contact with a water screen formed by spraying, using nozzles, pressurized circulating water, and for removing foreign materials from the air; a liquid separating part for separating from the air, tiny water droplets that are included in the air passing through the air-liquid contact part; a cylindrical body into which air to be cleaned is guided, and in which the air-liquid contact part and the liquid separating part are arranged in order; a chlorine dioxide addition unit, for adding a stabilized chlorine dioxide solution to a water tank for the water that is circulated; and a chlorine dioxide activation unit, for activating chlorine dioxide added to the circulating water, that is arranged in a circulating water pipe that extends from the water tank to the spray nozzles.

6 Claims, 3 Drawing Sheets

WATER SCREEN

AIR CLEANER

BACKGROUND OF THE INVENTION

1. Field of the Invention

The present invention relates to an air cleaner for cleaning air by removing visible or invisible foreign materials, for example, fine particles such as dust and cigarette smoke and various types of gases that produce bad odors, and airborne infectious microorganisms such as bacilli, molds and bacteria.

2. Related Arts

The air in various areas, including living and working spaces, differently sized assembly spaces and a variety of recreation locations such as pachinko parlors, and the compartments of transportation means such as vehicles, airplanes and ships, contains undesirable visible and invisible foreign materials, such as fine dust particles and cigarette smoke, various types of air pollutants, airborne infectious microorganisms and volatile organic gases generated by chemical materials, including adhesives and paints, and gases generated by human beings and a variety of manufactured products.

Most of these undesirable, fine particles and gases are harmful to human beings, and the content of these foreign materials in the air must be maintained at an extremely low level when processing is performed for super precision manufacturing devices and apparatuses, such as semiconductor devices, and the manufacture and processing of medical and pharmaceutical products, and in specific rooms in medical institutions. To satisfy this need, a so-called clean room is required, and for this, various air cleaning systems have been developed.

As a dry dust removal system, a downflow system is widely employed for clean rooms employed for the manufacture of semiconductor devices and integrated circuits. According to this system, air is passed through an extremely fine filter to adjust and to optimize temperature and humidity states. The air is then introduced into a room from the ceiling, and is discharged downward through a mesh floor. However, this dry dust removal system is effective only for the removal of solid dust, such as fine particles, but is less effective for gases. Further, the filter is easily clogged, and the initial characteristics can be maintained only for a short period of time. Also, when a finer filter is used, the frequency to perform the maintenance for the apparatus is increased.

On the other hand, another popular technique is one whereby, to clean the air, visible or invisible foreign materials, such as dust and gases, are removed by using water or another liquid. According to this technique, undesirable, fine particles and gases are removed from the air while the air is passed through water, or through a layer of fine water droplets that is formed by a water spray. This is a wet dust removal system technique that cleans the air by employing fine water droplets to dissolve fine particles and gases, through air-liquid contact, and uses the fine water droplets to remove the foreign materials.

It is known that not only is the air cleaning process performed during the air-liquid contact process, but that also during this cleaning process air bubbles are exploded and fine water droplets are separated to produce a large quantity of negative ions. As is well known, especially near forests and waterfalls there are many negative ions and they effectively act on human bodies, e.g., they are effective for recovering from fatigue and for physical and mental stabilization. Therefore, the air-liquid contact system that uses fine water droplets has drawn people's attention as an appropriate air cleaner for living spaces, working spaces such as offices and areas where many people assemble.

As a compact air cleaner developed for home use or office use, an air cleaner is disclosed in Japanese Patent Laid-Open Publication No. Hei 4-126717, for example, that comprises: a spray tower through which air to be cleaned is passed, while a pump is employed to spray pressurized water through nozzles; and a cyclone tower for rotating air after it has passed through the spray tower and discharging it to the outside. With this configuration, air introduced into the spray tower by a fan is cleaned, and following that, air obtained by air-liquid separation is discharged.

According to this air cleaner, when sprayed water and passing air contact each other in the spray tower, fine particles and contained gases are dissolved in the water, and thereafter, since water droplets collide with the wall face and are separated, finer water droplets are formed. Then, while an air stream formed of very fine water droplets is rotated within the cyclone tower, centrifugal force exerted on the air causes an air-liquid separation and clean air is discharged to the outside. However, with this arrangement, since the water spray resembles a shower ejected from an upright spray cylinder provided in the center of the spray tower, the efficiency with which the contact obtained between the water droplets and the air to be cleaned is less, and a satisfactory cleaning process can not be performed.

To resolve this shortcoming, disclosed in Japanese Patent Laid-Open Publication No. 2000-42338, for example, is another device wherein, in front of multiple spray nozzles, multiple, slightly displaced partitions (blocking plates) are formed and wherein a thick water screen layer is formed by the collision of sprayed water with these partitions, so that air to be cleaned passes through the water screen. Since, the air passes through the thus formed water screen after large dust particles have been removed from the air by a prefilter, a better air-liquid contact is obtained, thereby increasing the effects provided by the catching of fine particles and gases. However, since the partitions with which the sprayed water stream collides provide an air channel having only a narrow effective area, airflow resistance is increased, and accordingly, a fan having a larger capacity is required.

The use of a fan having a large capacity is not only contrary to the desired, energy saving objective, but is also contrary to the formation of a friendly environment because the fan generated noise is increased. While taking these facts into account, disclosed in Japanese Patent Laid-Open Publication No. 2002-119819, for example, is another device wherein multiple, opposing spray nozzles are provided in an air-liquid contact space and sprayed water particles collide with each other, forming a satisfactorily thick water screen without requiring the partitions (blocking plates) that can produce an increase in the airflow resistance.

According to this device, since two air-liquid spaces are arranged by using the opposing spray nozzles that are provided, a more effective air-liquid contact is ensured, and the capture of fine particles and gasses is more complete.

According to the above described configurations that use air-liquid contact, circulating water in a water tank is repeatedly employed for cleaning the air, and depending on the usage environment, the water becomes contaminated within a short period of time and produces a bad odor, so that the early cleaning of the water tank and the exchange of the water it contains are required. Furthermore, these conventional air cleaners do not provide the sterilization and deodorization processing required for the infectious microorganisms that are suspended in the air.

SUMMARY OF THE INVENTION

It is one objective of the present invention to provide an air cleaner that performs an air-liquid contact process that can pass air to be cleaned through a water screen, whereat to clean the air visible and invisible foreign substances are removed, and that can provide sterilization and deodorization effects by adding chlorine dioxide to water used to clean the air while circulating the water.

According to a first aspect of the present invention, an air cleaner comprises:

an air-liquid contact part 6, for bringing the air into contact with a water screen that is formed by spraying, through spray nozzles 13N, circulating water that is retained in a water tank 11 and is supplied under pressure, and for removing visible and invisible foreign materials from the air;

a liquid separating part 7, for separating, from the air, tiny water droplets that are included in the air that passes through the air-liquid contact part 6;

a cylindrical body 3 into which air to be cleaned is guided, and in which the air-liquid contact part 6 and the liquid separating part 7 are arranged in order;

a chlorine dioxide addition unit 16, for adding a stabilized chlorine dioxide solution to the water tank 11 for the water that is circulated; and a chlorine dioxide activation unit 20, for activating chlorine dioxide added to the circulating water, that is arranged in a circulating water pipe 13 that extends from the water tank 11 for the circulating water to the spray nozzles 13N located in the air-liquid contact part 6.

According to a second aspect of the present invention, the air-liquid contact part 6 is so located that distal ends of the spray nozzles 13N, used to spray water retained in the water tank 11, face each other in the direction in which air flows. Through collisions at the ends of water streams that are sprayed through the facing spray nozzles 13N, a thick water screen is formed that spreads across an airflow path in the cylindrical body 3, so that the air-liquid contact efficiency is increased. In this case, the water screen is a layer-like group of tiny water droplets generated by spraying water, and the thick water screen is indicative of a state wherein fine particles of water are present at a high density.

According to a third aspect of the present invention, the chlorine dioxide addition unit 16 employs a dropping method to add a predetermined volume of the chlorine dioxide solution, so as to provide a chlorine dioxide density of 100 ppm to 1000 ppm in the water tank 11. According to a fourth aspect of the present invention, a predetermined volume of the chlorine dioxide solution is added by the dropping method, so that a chlorine dioxide density of 200 ppm to 750 ppm is provided in the water tank 11.

According to a fifth aspect of the present invention, the chlorine dioxide activation unit 20 includes:

a liquid-sealed ultraviolet irradiation unit 22, arranged at an appropriate location along the circulating water pipe 13 extending from the water tank 11 to the spray nozzles 13N, for projecting an ultraviolet ray onto water circulating through the circulating water pipe 13. According to a sixth aspect of the present invention, an expanded portion (a portion having an extended pipe diameter) 21 is formed at one part of the circulating water pipe 13, and the ultraviolet irradiation unit 22 is positioned in the expanded portion 21 so as to project an ultraviolet ray onto circulating water in the expanded portion 21.

The chlorine dioxide used for this invention will now be explained. A chlorine dioxide ($ClO_2$) gas is an orange gas having a melting point of −95° C., a boiling point of 11° C. and a specific gravity of 2.33. 3.0 g/l of the chlorine dioxide gas is dissolved into water at 25° C., and 20 g/l is dissolved at 40° C.; however, since an industrial strength high-density chlorine dioxide solution is a strong oxidizer and may react with another material and produce high-density chloride or cause an explosion, this solution can not be used directly. Therefore, as a chlorine dioxide solution that presents no danger and is easily handled, a 5% stabilized chlorine dioxide solution is provided that has been developed by International Dioxide Inc. This solution is diluted in accordance with the usage. A chlorine dioxide gas produced by the evaporation of the stabilized chlorine dioxide solution is safe and does not generate strong irritating odors, and when this chlorine dioxide gas contacts an object, the chlorine dioxide gas becomes an effective medium for the sterilization, disinfection and deodorization of various types of bacteria, infectious microorganisms and molds.

As is described above, according to the invention, for an air cleaner wherein fine particles, infectious microorganisms and various gases that are suspended in air to be cleaned are captured by a liquid during an air-liquid contact process, during which the air is brought into contact with a water screen formed by spraying water, a stabilized chlorine dioxide solution is employed that provides sterilization and disinfection effects when added to the circulating water, and further, the chlorine dioxide activation unit is located along the pipe used for spraying the water.

Therefore, as the air cleaning operation continues, clean, circulating water retained in the water tank absorbs befouling organisms, consisting of fine particles and gases in the air, and is gradually contaminated and may generate a bad odor. However, since chlorine dioxide that is added to the circulating water and is activated by ultraviolet irradiation provides sterilization and deodorization, the spreading of airborne infectious microorganisms and the generation of bad odors can be prevented. With the above described configuration of the air cleaner, the time whereat the cleaning function deteriorates can be delayed as long as possible, and until this time, many negative ions can be generated. Thus, superior air conditioning is enabled by adjusting the temperature and the humidity of clean air that contains many negative ions.

Furthermore, according to the air cleaner of the invention, the air-liquid contact part can appropriately employ the configuration wherein a thick water screen is formed by the collision of the ends of water streams sprayed from the spraying nozzles, so that the water screen extends across the cylindrical body.

Therefore, while the air to be cleaned is passed through the thick water screen, the air-liquid contact occurs at an extremely high efficiency, and visible and invisible foreign materials in the air, such as dust, airborne infectious microorganisms, cigarette smoke and other contaminants, are captured and removed from the air by the circulating water. In addition, while the water is separated into fine water drops through the collision of the sprayed water and the collision of the sprayed water with the walls of the cylindrical body, negative ions are generated. These negative ions are mixed with clean air and are discharged into the clean air space.

DETAILED DESCRIPTION OF THE PREFERRED EMBODIMENT

The present invention relates to an air cleaner that removes visible and invisible foreign materials in an air-liquid contact process during which air to be cleaned contacts a water screen, and that can provide sterilization and deodorization effects by the addition of chlorine dioxide to circulating water that is used for cleaning air.

An explanation will be given for the preferred embodiment of the present invention while referring to the accompanying drawings; however, the present invention is not limited to this embodiment.

Figure 1:
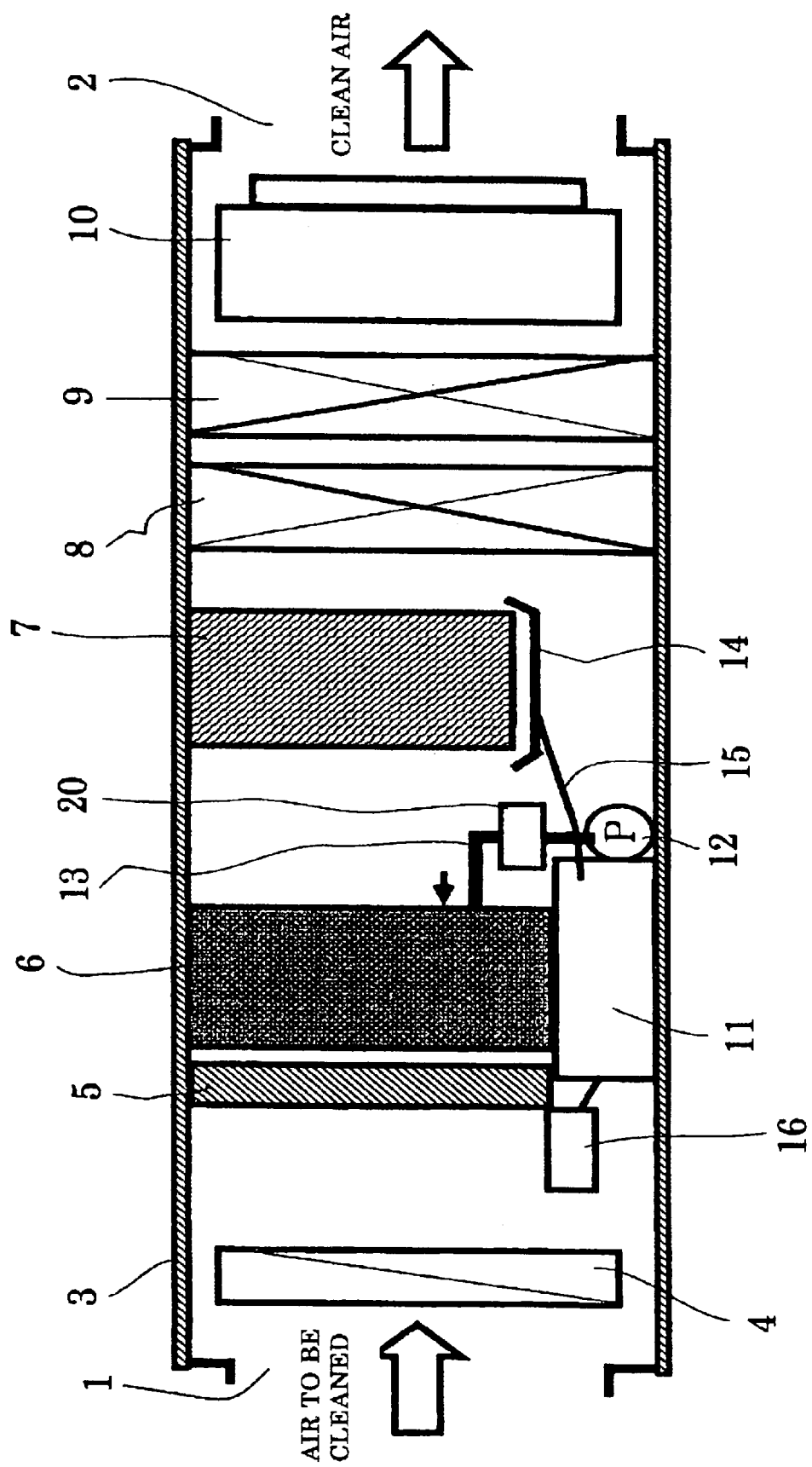
FIG. 1 is a side cross-sectional view showing an example air cleaner configuration according to the present invention.

An air cleaner according to the embodiment of the invention will now be described while referring to the accompanying drawings. FIG. 1 is a diagram showing the general configuration of the air cleaner according to the embodiment of the invention. In a horizontally extended cylindrical body 3, wherein an intake port 1 is formed at one end and an delivery port 2 is formed at the other end, are arranged a prefilter 4, a louver 5, an air-liquid contact part 6, a liquid separating part 7, a cooling coil 8 and a heating coil 9, beginning with the one nearest the intake port 1, and an air supply fan 10 is arranged at the end near the delivery port 2.

The cylindrical body 3 is a duct that forms a path along which external air to be cleaned flows through the intake port 1, and the delivery port 2 is an opening through which clean air is delivered outside the cylindrical body 3. In this embodiment, for the convenience of the explanation, the cylindrical body 3 is a straight-tube duct; however, a bent-tube or curved-tube duct may be employed so long as the airflow is not restricted. Further, in this embodiment, an inducing fan is employed as the air supply fan 10 and is arranged at the end near the delivery port 2. However, a forcing fan may be employed at the end near the intake port 1, or two fans may be provided, i.e., a forcing fan at the end near the intake port 1, and an inducing fan at the end near the delivery port 2.

The prefilter 4 is used to filter the external air taken in through the intake port 1, and to remove dust having a large particle diameter from the air. The louver 5 is used to prevent water droplets formed by the air-liquid contact port 6 from reversely flowing toward the intake port 1.

The air-liquid contact part 6 employs a pump 12 to feed, under pressure, water from a water tank 11 in which circulating water is retained, and sprays water through nozzles 13N (see FIG. 3) to form a water screen that extends across a path along which air to be cleaned flows. The air-liquid contact part 6, in order to remove foreign materials from the air, brings the flowing air into contact with the water screen, and dissolves in water dust and other fine particles, airborne infectious microorganisms and gases contained in the air. Many configurations and combinations of them can be employed to form the water screen and to perform the air-liquid contact process.

The liquid separating part 7 separates fine water droplets from the air that has passed through the air-liquid contact part 6. The liquid separating part 7 can be a separation unit for collecting the fine water droplets and forming large droplets that are removed by gravity, or a separation unit for employing centrifugal force while rotating an air stream in which fine water droplets are included. It should be noted that a tray 14 for accepting separated water droplets is provided at the lowermost portion of the liquid separating part 7, and that the water droplets that have been separated from the air are returned to the water tank 11 through a drain pipe 15.

A stabilized chlorine dioxide addition unit 16, arranged adjacent to the water tank 11, adds a stabilized chlorine dioxide ($ClO_2$) solution to the water as it is circulated in order to sterilize and deodorize it. Further, a chlorine dioxide activation unit 20 is located at an appropriate position along a pipe 13 through which water is fed from the pump 12 to the air-liquid contact part 6. The stabilized chlorine dioxide addition unit 16 and the chlorine dioxide activation unit 20 will be described later while referring to FIG. 2.

The cooling coil 8 and the heating coil 9 in FIG. 1, which are the same as those used for an ordinary air conditioner, are respectively connected to a cooling source and a heating source (not shown) to cool or heat air as it passes through, and to thus perform an air conditioning function. Since the air conditioning function can be provided by combining well known apparatuses, no detailed explanation for this function will be given.

Figure 2:
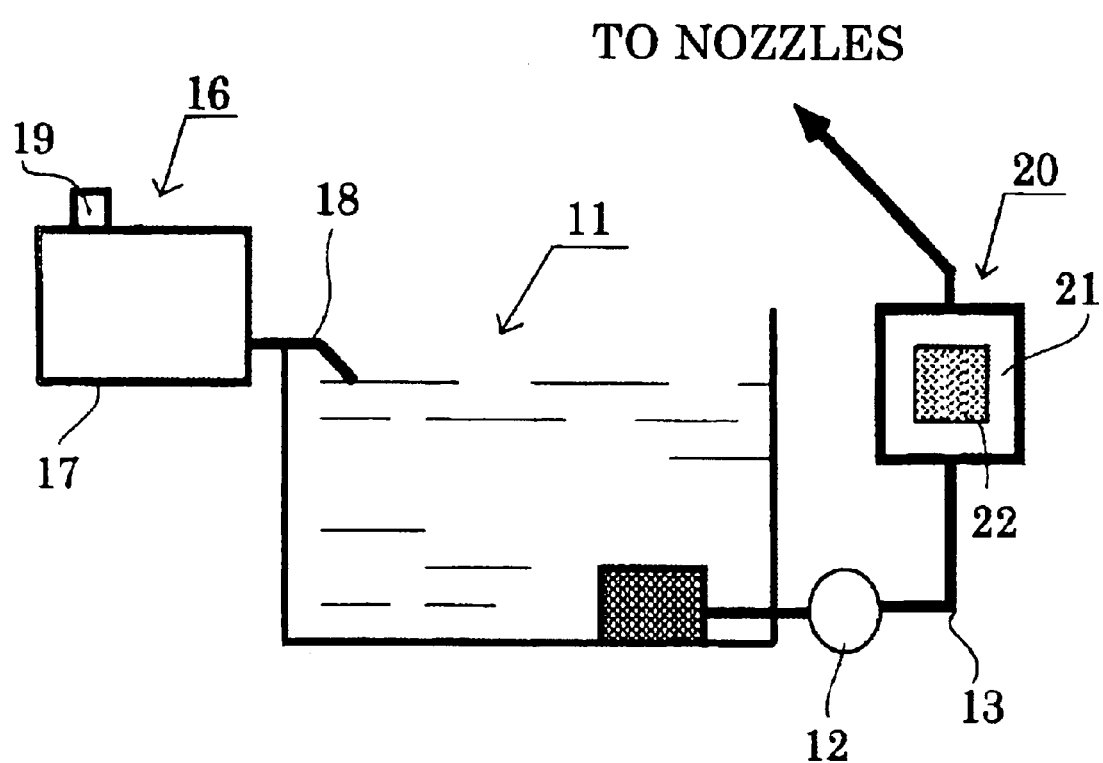
FIG. 2 is a diagram showing an example arrangement for a water tank, a chlorine dioxide addition unit and a chlorine dioxide activation unit for the air cleaner according to the present invention.

FIG. 2 is a diagram showing the state wherein the stabilized chlorine dioxide addition unit 16 and the chlorine dioxide activation unit 20, which together constitute the feature of the invention, are arranged relative to the water tank 11, the pump 12 and the pipe 13 shown in FIG. 1 for the sterilization and deodorization of the air and the circulating water. Provided for the water tank 11 are a supplement tank 17 for supplying a stabilized chlorine dioxide solution from above and a falling-drop pipe 18, along which the stabilized chlorine dioxide solution flows and is added to the circulating water that is supplied from the bottom of the water tank 11.

The position of the stabilized chlorine dioxide addition unit 16, which includes the supplement tank 17 and the falling-drop pipe 18 for the stabilized chlorine dioxide solution, is not especially limited, so long as the distal end of the falling-drop pipe 18 reaches the inside of the water tank 11. The stabilized chlorine dioxide addition unit 16 can be located at an arbitrary position, so long as the position and the configuration do not interfere with the flow of the air to be cleaned and the functions required for cleaning the air, such as the air-liquid contact function and the liquid separation function. Furthermore, a stabilized chlorine dioxide solution supplement port 19 for the supplement tank 17 should be positioned while taking the operability into account, so that the supply of the stabilized chlorine dioxide solution can be easily supplemented from the outside.

In this embodiment, the density of chlorine dioxide is 100 to 1000 ppm, but preferably is 200 to 750 ppm, and more preferably, is 400 to 600 ppm; however, the density can be adjusted in accordance with the installation environment. The stabilized chlorine dioxide addition unit 16 can be turned on or off, depending on the operation of the air cleaner. However, depending on the usage environment, the ON/OFF state and the operating state may be adjusted separately from the state of the main body of the air cleaner.

The chlorine dioxide activation unit 20 is located at an appropriate position along the pipe 13 extending from the nozzles 13N to the pump 12, which extracts, using suction, circulating water from the water tank 11 and feeds it to the pipe 13 and the nozzles 13N under pressure. In addition, for the chlorine dioxide activation unit 20, an expanded portion (a pipe having a larger diameter) 21, having a cylindrical or polygonal cross section, is located at an appropriate position along the pipe 13, and a liquid-sealed ultraviolet irradiation unit 22 is provided inside the expanded portion 21.

To activate chlorine dioxide, it is generally effective for an ultraviolet ray to be projected, by an ultraviolet generator, directly into an air stream that contains a chlorine dioxide solution. However, a partition consisting of an ultraviolet transmitting material may be formed, and an ultraviolet ray may be projected into an air stream through this partition. In the configuration wherein the chlorine dioxide solution directly contacts the ultraviolet irradiation unit, only a completely waterproof fluorescent chemical lamp need be employed as the ultraviolet irradiation unit.

The chlorine dioxide activation unit 20 incorporating the ultraviolet irradiation unit can include a temperature adjustment unit, a projected ultraviolet volume adjustment unit and a time controller (timer), and can cope with a loading condition that changes, depending on the conditions, such as the number of occupants in an object space (place), the temperature, the humidity, the quantity of heat that is generated based on the load and the usage time period. These adjustments and controls can be performed by additionally providing well known control devices or apparatuses, such as a program timer, a thyristor controller and an ultraviolet filter. Furthermore, not only can the chlorine dioxide activation unit 20 be operated by interlocking with the main body and the stabilized chlorine dioxide addition unit 16, but also the control of the ON/OFF state and the adjustment of the operating state can be independently performed.

With this configuration, a stabilized chlorine dioxide having an appropriate density is added by the chlorine dioxide addition unit 16. And the chlorine dioxide that is contained in each of the fine water droplets of the water screen formed in the air-liquid contact part 6 can be activated by the chlorine dioxide activation unit 20. During the air-liquid contact process, this chlorine dioxide acts on airborne infectious microorganisms and various bacteria that are contained in the air to be cleaned, and provides sterilization and deodorization effects. As a result, not only a solid material, such as tiny dust particles, but also various infectious microorganisms, bacteria and molds can be removed or rendered harmless, so that a real air cleaning function can be expected.

Figure 3:
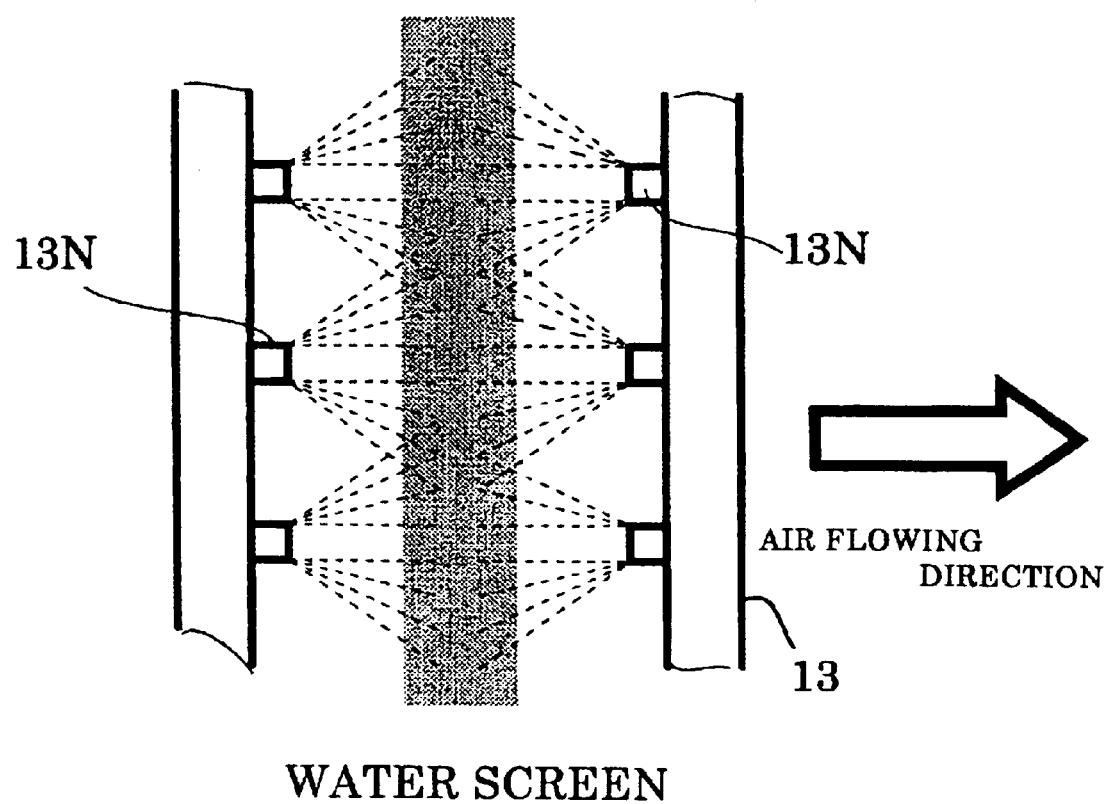
FIG. 3 is a diagram for explaining the process for forming a water screen in the air-liquid contact part of the air cleaner according to the present invention.

FIG. 3 is a side view of an example configuration for the nozzles 13N that, to efficiently form a water screen in the air-liquid contact part 6, are arranged facing each other. To form a spray nozzle 13N, a spray opening is formed in each of a number of lattice-shaped or mesh shaped frames made of a pipe material and a branch pipe, and to supply water, an appropriate number of the spray nozzles 13N are arranged along the distal end of the pipe 13. The shape of the spray nozzles 13N and the number of these nozzles 13N can be selected, and depends on the size of the apparatus and the usage. A satisfactory water screen can be formed by providing this nozzle structure only on one side. However, as is shown in FIG. 3, when the spray ports of the nozzles 13N are vertically positioned facing each other, in the airflow direction indicated by an arrow, and the ends of the water streams sprayed from both sides collide with each other, a thick water screen can be formed that intersects the air flowing in the indicated direction.

To use the air cleaner according to the invention, a predetermined quantity of water is used to fill the water tank 11 in advance, the chlorine dioxide addition unit 16 adds a stabilized chlorine dioxide solution to provide a predetermined density, e.g., 100 to 1000 ppm, and the chlorine dioxide activation unit 20 is activated. Then, the pump 12 for circulating the water is driven and water is fed, under pressure, to the pipe of the air-liquid contact part 6. When the pressurized water arrives at the nozzles 13N arranged in a lattice shape or as an array, the water is sprayed from the nozzles 13N and the ends of the water streams sprayed in opposite directions collide with each other, forming a thick water screen that entirely covers the water spraying faces. The range of this water screen, and its thickness, can be arbitrarily adjusted by controlling the interval between the facing nozzles 13N, the nozzle diameters and the water feeding pressure.

When the fan 10 is driven while the water screen is thus being formed, air to be cleaned is drawn in through the intake port 1 by suction. While the air drawn into the cylindrical body 3 passes through the prefilter 4, large dust particles are removed, and then, the air flows through the louver 5, which controls the airflow direction, and to the air-liquid contact part 6. Since the water screen formed in the air-liquid contact part 6 extends across the entire path along which the air flows through the contact part 6, the air penetrates and passes through the water screen and efficient air-liquid contact is ensured.

As a result, not only fine, visible particles, but also cigarette smoke, gases and airborne infectious microorganisms, all of which are carried by the air stream that has passed through the prefilter 4, are captured by the fine water droplets, and air cleaning, sterilization and deodorization are performed. The air stream, which has passed through the air-liquid contact part 6 and includes fine water droplets, then flows on to the liquid separating part 7.

Since in the liquid separating part 7 the air that includes the fine water droplets collides with the separation plate, the fine water droplets are removed by gravity and centrifugal force. Then, the air obtained by the cleaning and liquid separation processes is cooled or heated while passing through the cooling coil 8 or the heating coil 9, whichever has been selectively activated in accordance with the situation. The resultant clean air is then delivered, through the delivery port 2, to the space that is being air conditioned.

According to the air cleaner according to the invention, since the structure and the arrangement of the nozzles 13N in the air-liquid contact part 6 are taken into account, tiny water droplets can be obtained, and a thick water screen can be formed. Therefore, more efficient air-liquid contact is ensured. Furthermore, since the activated chlorine dioxide solution is added to the circulating water used to form the water screen, not only are dust and other fine particles efficiently removed from the air, but also the effects produced by sterilization and deodorization are provided to remove bacilli, bacteria and other airborne infectious microorganisms. Therefore, real air cleaning is enabled, so that when the thus arranged air cleaner and an air conditioner are employed together, an environment is provided with clean air from which not only solid material, such as fine dust, and gases, but also bacilli and bacteria have been removed.

According to the air cleaner according to the invention, the effects of sterilization and deodorization can be provided for visible and invisible airborne foreign materials, including, for example, dust and other fine particles, airborne infectious microorganisms such as bacilli and bacteria, and undesirable gases, so that satisfactory air cleaning can be performed. This air cleaner can also perform effectively as an air cleaner for a super clean room and an ultra clean room for which stricter conditions are required.

Further, since outstanding sterilization and deodorization effects are provided to remove bacilli, bacteria and viruses, the air cleaner of the invention is also an effective means for preventing the spread of various types of airborne infections. In addition, since negative ions are produced when the tiny water droplets are broken, excellent effects can also be provided for recovering from exhaustion and for physical and mental stabilization. Therefore, the air cleaner of the invention is appropriate for use in various medical institutions and for air conditioned facilities for which the strict management of the environment is required.

Various other modes of carrying out the invention are contemplated that are within the scope of the following claims that in particular point out and distinctly describe the subject matter regarded as the invention.

What is claimed is:

1. An air cleaner comprising:
   an air-liquid contact part, for bringing the air into contact with a water screen that is formed by spraying, through spray nozzles, circulating water that is retained in a water tank and is supplied under pressure, and for removing visible and invisible foreign materials from the air;
   a liquid separating part, for separating, from the air, tiny water droplets that are included in the air that passes through the air-liquid contact part;
   a cylindrical body into which air to be cleaned is guided, and in which the air-liquid contact part and the liquid separating part are arranged in order;
   a chlorine dioxide addition unit, for adding a stabilized chlorine dioxide solution to the water tank for the water that is circulated; and
   a chlorine dioxide activation unit, for activating chlorine dioxide added to the circulating water, that is arranged in a circulating water pipe that extends from the water tank for the circulating water to the spray nozzles located in the air-liquid contact part.

2. An air cleaner according to claim 1, wherein the air-liquid contact part is so located that distal ends of the spray nozzles, used to spray water retained in the water tank, face each other in the direction in which air flows; and wherein, through collisions at the ends of water streams that are sprayed through the facing spray nozzles, a thick water screen is formed that spreads across an airflow path in the cylindrical body, so that air-liquid efficiency is increased.

3. An air cleaner according to claim 1, wherein the chlorine dioxide addition unit employs a dropping method to add a predetermined volume of the chlorine dioxide solution, so as to provide a chlorine dioxide density of 100 ppm to 1000 ppm in the water tank.

4. An air cleaner according to claim 1, wherein a predetermined volume of the chlorine dioxide solution is added by the dropping method, so that a chlorine dioxide density of 200 ppm to 750 ppm is provided in the water tank.

5. An air cleaner according to claim 1, wherein the chlorine dioxide activation unit includes:
   a liquid-sealed ultraviolet irradiation unit, arranged at an appropriate location along the circulating water pipe extending from the water tank to the spray nozzles, for projecting an ultraviolet ray onto water circulating through the circulating water pipe.

6. An air cleaner according to claim 5, wherein an expanded portion is formed at one part of the circulating water pipe, and the ultraviolet irradiation unit is positioned in the expanded portion so as to project an ultraviolet ray onto circulating water in the expanded portion.

* * * * *